US008183298B2

(12) United States Patent
Issberner et al.

(10) Patent No.: US 8,183,298 B2
(45) Date of Patent: May 22, 2012

(54) FATTY ACID ESTERS, PROCESSES FOR THEIR PRODUCTION AND FOR INCORPORATION INTO COSMETIC AND/OR PHARMACEUTICAL FORMULATIONS

(75) Inventors: Ulrich Issberner, Rommerskirchen (DE); Catherine Weichold, Aachen (DE); Achim Ansmann, Erkrath (DE); Stefan Bruening, Philadelphia, PA (US); Helga Gondek, Duesseldorf (DE)

(73) Assignee: Cognis IP Management GmbH, Dusseldorf (DE)

( * ) Notice: Subject to any disclaimer, the term of this patent is extended or adjusted under 35 U.S.C. 154(b) by 172 days.

(21) Appl. No.: 10/599,682

(22) PCT Filed: Mar. 26, 2005

(86) PCT No.: PCT/EP2005/003234
§ 371 (c)(1),
(2), (4) Date: Jul. 30, 2007

(87) PCT Pub. No.: WO2005/097044
PCT Pub. Date: Oct. 20, 2005

(65) Prior Publication Data
US 2008/0051470 A1 Feb. 28, 2008

(30) Foreign Application Priority Data
Apr. 5, 2004 (DE) .......... 10 2004 017 222

(51) Int. Cl.
*A61K 47/00* (2006.01)
*A61K 8/02* (2006.01)
*C07C 69/34* (2006.01)

(52) U.S. Cl. ....... 514/785; 424/401; 424/69; 424/70.19; 560/190; 528/425

(58) Field of Classification Search ............ 510/475; 424/69, 70.11, 70.19, 365, 401
See application file for complete search history.

(56) References Cited

U.S. PATENT DOCUMENTS

| 1,951,593 | A | * | 3/1934 | Bradley | .......... 528/308 |
| 2,427,255 | A | * | 9/1947 | Burrell et al. | .......... 106/243 |
| 2,441,555 | A | * | 5/1948 | Barth et al. | .......... 554/227 |
| 2,705,722 | A | * | 4/1955 | Barsky | .......... 554/182 |
| 2,975,152 | A | * | 3/1961 | Beavers et al. | .......... 524/356 |
| 3,976,789 | A | | 8/1976 | Tomita et al. | |
| 4,113,635 | A | * | 9/1978 | Sakurai et al. | .......... 508/312 |
| 4,290,337 | A | | 9/1981 | Kuwata et al. | |
| 4,332,702 | A | * | 6/1982 | Lindner | .......... 524/178 |
| 4,868,220 | A | * | 9/1989 | Scheuffgen | .......... 514/784 |
| 5,304,665 | A | * | 4/1994 | Cooper et al. | .......... 554/149 |
| 5,374,716 | A | | 12/1994 | Biermann et al. | |
| 5,436,006 | A | * | 7/1995 | Hirose et al. | .......... 424/401 |
| 5,576,425 | A | | 11/1996 | Hill et al. | |
| 5,654,312 | A | * | 8/1997 | Andrulis et al. | .......... 514/279 |
| 5,741,919 | A | | 4/1998 | O'Lenick et al. | |
| 6,432,419 | B2 | * | 8/2002 | Kahre et al. | .......... 424/401 |
| 6,939,980 | B2 | * | 9/2005 | Memita et al. | .......... 554/170 |
| 2003/0118621 | A1 | | 6/2003 | Heidenfelder et al. | |
| 2004/0258721 | A1 | | 12/2004 | Bauer et al. | |

FOREIGN PATENT DOCUMENTS

| EP | 0035729 | * | 9/1981 |
| EP | 0 163 806 | | 12/1985 |
| EP | 0163806 | * | 12/1985 |
| EP | 0 179 416 | | 4/1986 |
| EP | 0179416 | * | 4/1986 |
| EP | 0 301 298 | | 2/1989 |
| EP | 1 290 999 | | 3/2002 |
| EP | 1 216 685 | | 6/2002 |
| JP | 50-008804 A | | 1/1975 |
| JP | 56-152801 A | | 11/1981 |
| WO | WO 90/03977 | | 4/1990 |
| WO | WO 99/62468 | | 12/1999 |
| WO | WO 03/028690 | | 4/2003 |

OTHER PUBLICATIONS

Konthe, G. et al. Biodiesel: The Use of Vegetable Oils and Their Derivates as Alterantives Diesel Fuels, 1997, American Chemical Society, pp. 173-207.*
Konen, J.C. et al., Esterificaion of Unsaturated Fatty Acids, 1945, Oil & Soap, vol. 22, pp. 57-60.*
Kirk-Othmer, Encyclopedia of chemical technology, 1993, Wiley-Interscience Publication, vol. 10, 4th ed., 3 pages.*
JP 50-008804, Sakurai, T. et al, Lubricating oil composition for metal plastic working, Jan. 29, 1973, English Translation, (25 pages) cover and pp. 1-24.*
EP 0035729, Henkel DGAA, Radical polymerization and synthetic substance additive, Nov. 26, 1981, English Translaiton, (5 pages).*
Breusch et al., "Darstellung der di-, tri- und tetra-homologen Reihen der Methan-methylol-fettsaeureester (XIV.Mitteil. ueber isomere und homologe Reihen)", Chem. Ber., 1955, vol.88, pp. 1511-1519. XP009051613.
Gassenmeier et al., "Sensory Assessment of Lipids in Leave-On and Rinse-Off Products", Cosmetic Lipids and the Skin Barrier, Marcel Dekker, 2002, pp. 319-352.

* cited by examiner

*Primary Examiner* — Yate K Cutliff
(74) *Attorney, Agent, or Firm* — Diehl Servilla LLC

(57) ABSTRACT

A fatty acid ester of pentaerythritol, a pentaerythritol oligomer, or mixtures thereof, where the fatty acid has 6 to 22 carbon atoms, and the ester contains less than 0.3% by weight $C_{17}$ fatty acid acyl groups and has a melting point of at least 30° C. is provided. A process for the production of a $C_{16}/C_{18}$ fatty acid pentaerythritol ester including (A) providing about 1.8 to about 2.2 mol of a fatty acid mixture per mol of pentaerythritol; (B) esterifying component (A) at temperatures ranging from about 180° C. to about 250° C. in an inert gas atmosphere in the absence of solvent to form a reaction mixture; (C) stirring the reaction mixture in vacuo until it has an acid value of less than 1 and an OH value of 145 to 158 is provided. A cosmetic and/or pharmaceutical composition including the above-described ester is also provided.

14 Claims, No Drawings

FATTY ACID ESTERS, PROCESSES FOR THEIR PRODUCTION AND FOR INCORPORATION INTO COSMETIC AND/OR PHARMACEUTICAL FORMULATIONS

RELATED APPLICATIONS

This application is a national phase filing under 35 U.S.C. §371 and claims priority to International Application No. PCT/EP2005/003234 which has an international filing date of Mar. 26, 2005, and which designated the United States of America and which claims priority to German Application No. 10 2004 017 222.6, filed Apr. 5, 2004, the entire disclosures of which are hereby incorporated herein by reference.

FIELD OF THE INVENTION

This invention relates generally to fatty acid esters, and more particularly to wax-like fatty acid esters of pentaerythritol or oligomers of pentaerythritol, a process for their production, and a cosmetic and/or pharmaceutical composition containing same.

BACKGROUND INFORMATION

Wax-based formulations have long been known to the expert and are used inter alia for cosmetic and pharmaceutical formulations, such as suppositories for example, various cosmetic compositions in stick form or in creams and lotions, for coating papers and textiles, etc. Numerous wax-like substances and mixtures of such substances are available to the expert for this purpose. These include, for example, glycerides and fatty alcohols which have a critical effect on the sensory profile of the final formulations. Thus, glycerides leave the skin with an often oily/greasy feeling. Fatty alcohols lead to the formation of white residues which users find to be a major disadvantage. Silicone oils are often added to counteract formation of the white residues. Silicone oils are also used to reduce the tackiness of the formulations and to improve their smooth, velvety feeling on the skin. Unfortunately, some silicone oils have toxicological and ecological disadvantages. Because of this, silicone oil substitutes have been sought for some time.

The problem addressed by the present invention was to provide wax-like substances and compositions based on those substances which would afford additional sensory advantages—usually achieved by silicone oils—over the waxes normally used. Such waxes would enable cosmetic preparations free from silicone oils to be formulated without losing the typical sensory profile unique to silicone oils.

It has now surprisingly been found that these properties can be achieved by special waxes based on pentaerythritol or oligomers thereof which are produced from vegetable rather than animal raw material sources.

Pentaerythritol esters have long been on the market and are used inter alia as emulsifiers in the food industry. These esters emanate from animal raw material sources. The product marketed by Cognis Deutschland GmbH & Co. KG under the name of Loxiol® P 728 is mentioned purely by way of example in this regard. It contains ca. 2% by weight $C_{17}$ fatty acids and has a $C_{16}/C_{18}$ distribution of ca. 30:70 and thus corresponds to other commercially available products. Unfortunately, wax esters such as these are not entirely satisfactory in regard to stability, viscosity, macroscopic/microscopic appearance or in regard to the sensory profile of the cosmetic compositions produced with them.

SUMMARY OF THE INVENTION

According to an aspect of the invention, a fatty acid ester of pentaerythritol, a pentaerythritol oligomer, or mixtures thereof is described, where the fatty acid has 6 to 22 carbon atoms, and the ester contains less than 0.3% by weight $C_{17}$ fatty acid acyl groups and has a melting point of at least 30° C.

According to another aspect of invention, a process for the production of a $C_{16}/C_{18}$ fatty acid pentaerythritol ester includes the steps of: (A) providing about 1.8 to about 2.2 mol of a fatty acid mixture per mol of pentaerythritol where the fatty acid mixture comprises from about 40% to about 50% by weight of a $C_{16}$ fatty acid and from about 45% to about 55% by weight of a $C_{18}$ fatty acid; (B) esterifying component (A) at temperatures ranging from about 180° C. to about 250° C. in an inert gas atmosphere in the absence of solvent to form a reaction mixture; (C) stirring the reaction mixture in vacuo until it has an acid value of less than 1 and an OH value of 145 to 158.

In another aspect of the invention, a cosmetic and/or pharmaceutical composition includes an ester formed by esterification of pentaerythritol, a pentaerythritol oligomer, or mixtures thereof with $C_{6-22}$ fatty acids, where the ester contains less than 0.3% by weight $C_{17}$ fatty acid acyl groups and has a melting point of at least 30° C.

DETAILED DESCRIPTION OF THE INVENTION

Accordingly, the present invention relates to esters of $C_{6-22}$ fatty acids of pentaerythritol and/or dipentaerythritol, tripentaerythritol which contain less than 0.3% by weight $C_{17}$ fatty acid acyl groups and have a melting point of at least 30° C. It has surprisingly been found that these esters have a very good sensory property profile in cosmetic compositions.

The esters may contain a single type of fatty acid acyl groups or a mixture of various fatty acid acyl groups; the fatty acids may be branched or unbranched and/or saturated or unsaturated. Fatty acids with a large content of saturated unbranched fatty acids, particularly those emanating from vegetable raw material sources, are preferably used for the esterification. According to the invention, $C_{14-24}$ fatty acids and particularly $C_{14-20}$ fatty acids are preferred. A preferred embodiment of the invention are esters of pentaerythritol with a percentage content of (a) 5 to 35% by weight monoesters, (b) 20 to 50% by weight diesters and (c) 25 to 50% by weight triesters and optionally tetraesters. A content of (a) 10 to 25% by weight monoesters, (b) 25 to 40% by weight diesters and (c) 30 to 45% by weight triesters and optionally tetraesters is preferred while a content of (a) 12 to 19% by weight monoesters, (b) 25 to 35% by weight diesters, (c) 30 to 40% by weight triesters and (d) 6 to 11% by weight tetraesters is most particularly preferred.

Another preferred embodiment of the esters is characterized in that a fatty acid mixture containing 40 to 50% by weight $C_{16}$ fatty acid and 45 to 55% by weight $C_{18}$ fatty acid is used for the esterification. The rest of the fatty acid mixture is made up of relatively short-chain ($\leq C_{14}$) and relatively long-chain ($>C_{18}$) fatty acids. Esters of pentaerythritol and dipentaerythritol with a ratio by weight of $C_{16}/C_{18}$ fatty acids of ca. 0.7 to 0.9 are superior in terms of sensory properties. According to the invention, a particularly suitable ester is an ester of pentaerythritol which is obtained by reaction of pentaerythritol with a fatty acid mixture containing 42 to 48% by weight $C_{16}$ fatty acid and 50 to 56% by weight $C_{18}$ fatty acid (rest $\leq C_{14}$ fatty acids and $>C_{18}$ fatty acids) and which has the following ester distribution: 12 to 19% by weight monoester, (b) 25 to 35% by weight diester, (c) 30 to 40% by weight triester and (d) 6 to 11% by weight tetraester. Normally, 1.8 to 2.2 mol and, preferably, 1.9 to 2.1 mol of the fatty acid mixture per mol pentaerythritol is used for the esterification.

The present invention also relates to a process for the production of $C_{16}/C_{18}$ fatty acid pentaerythritol esters in which 1.8 to 2.2 mol and, preferably, 1.9 to 2.1 mol per mol pentaerythritol of a fatty acid mixture containing 40 to 50% by weight $C_{16}$ fatty acid and 45 to 55% by weight $C_{18}$ fatty acid or a raw material mixture with a corresponding fatty acid distribution is used and (a) the esterification is carried out at temperatures of 180° C. to 250° C. in an inert gas atmosphere in the absence of solvent, (b) the water formed is distilled off, (c) the reaction mixture obtained is stirred in vacuo until it has an acid value of <1 and an OH value of 145 to 158, (d) unreacted pentaerythritol is filtered off and (e) an aftertreatment with hydrogen peroxide is optionally carried out. Methods for monitoring and adjusting acid value and OH value are well-known to the expert, so that there is no need to discuss them in detail here.

The present invention also relates to the use of the esters according to the invention as consistency factors.

Commercial Applications

Cosmetic and pharmaceutical compositions containing the esters according to the invention as constituents are superior to similar known compositions in regard to stability, viscosity, macroscopic/microscopic appearance and/or in regard to sensory profile. They are easy to apply and spread, are readily absorbed by the skin and leave it feeling smooth and velvety rather than oily, sticky or greasy.

Accordingly, the present invention also relates to cosmetic and/or pharmaceutical compositions containing the esters according to the invention, preferably in a quantity of 0.1 to 20% by weight, based on the composition as a whole. According to the invention, particularly suitable compositions contain esters of pentaerythritol which are obtained by reaction of pentaerythritol with a fatty acid mixture containing 42 to 48% by weight $C_{16}$ fatty acid and 50 to 56% by weight $C_{18}$ fatty acid (rest $\leq C_{14}$ fatty acids and $>C_{18}$ fatty acids) and which have the following ester distribution: 12 to 19% by weight monoesters, (b) 25 to 35% by weight diesters, (c) 30 to 40% by weight triesters and (d) 6 to 11% by weight tetraesters. These compositions have a particularly good property profile in regard to stability, viscosity, macroscopic/microscopic appearance and in regard to sensory profile. A preferred embodiment of the composition according to the invention is free from silicone oils. The present invention also relates to the use of the composition according to the invention for body care.

Other Wax Components

Another preferred embodiment of the invention contains at least one other wax component. Waxes are normally understood to be any natural or synthetic substances and mixtures having the following properties: they have a solid to brittle hard consistency, are coarsely to finely crystalline, transparent to opaque and melt above 30° C. without decomposing. Even slightly above their melting point, they are low in viscosity and non-stringing and are very temperature-dependent in their consistency and solubility. A wax component or a mixture of wax components which melt(s) at 30° C. or higher may be used in accordance with the invention. They are present in the compositions according to the invention in a total quantity of 0.1 to 15% by weight. In a preferred embodiment of the invention, the content of additional wax component(s) is from 0.1 to 10% by weight, preferably from 0.5 to 5% by weight and more particularly from 1 to 5% by weight, based on the composition as a whole.

According to the invention, fats and fat-like substances with a wax-like consistency may also be used as waxes, providing they have the required melting point. These include inter alia fats (triglycerides), mono- and diglycerides, natural and synthetic waxes, fatty and wax alcohols, fatty acids, esters of fatty alcohols and fatty acids and also fatty acid amides or mixtures of these substances.

Fats in the context of the invention are understood to be triacylglycerols, i.e. the triple esters of fatty acids with glycerol. They preferably contain saturated, unbranched and unsubstituted fatty acid components. They may also be mixed esters, i.e. triple esters of glycerol with various fatty acids. So-called hardened fats and oils obtained by partial hydrogenation may be used in accordance with the invention and are particularly suitable as consistency factors. Vegetable hardened fats and oils, for example hardened castor oil, peanut oil, soybean oil, colza oil, rapeseed oil, cottonseed oil, soybean oil, sunflower oil, palm oil, palm kernel oil, linseed oil, almond oil, corn oil, olive oil, sesame oil, cocoa butter and coconut fat, are preferred.

Suitable fats are inter alia the triple esters of glycerol with $C_{12-60}$ fatty acids and in particular $C_{12-36}$ fatty acids. These include hydrogenated castor oil, a triple ester of glycerol and a hydroxystearic acid which is marketed, for example, under the name of Cutina® HR. Glycerol tristearate, glycerol tribehenate (for example Syncrowax® HRC), glycerol tripalmitate or the triglyceride mixtures known under the name of Syncrowax® HGLC, are also suitable providing the melting point of the wax component or the mixture as a whole is 30° C. or higher.

According to the invention, other suitable wax components are mono- and diglycerides and mixtures of these partial glycerides. Glyceride mixtures suitable for use in accordance with the invention include the products Novata® AB and Novata® B (mixture of $C_{12-18}$ mono-, di- and triglycerides) and Cutina® MD or Cutina® GMS (glyceryl stearate) marketed by Cognis Deutschland GmbH & Co. KG. According to the invention, $C_{12-24}$ partial glycerides are particularly suitable as the other wax component.

Mixed esters and mixtures of mono-, di- and triglycerides are particularly suitable for the purposes of the invention because they have a relatively low tendency towards crystallization and thus improve the performance of the composition according to the invention. In addition, they show considerably better compatibility with oils of widely varying polarity.

Fatty alcohols suitable for use in accordance with the invention include $C_{12-50}$ fatty alcohols. According to the invention, $C_{12-24}$ fatty alcohols are particularly suitable as the other wax component and may even be used in combination with the $C_{12-24}$ partial glycerides. The fatty alcohols may be obtained from natural fats, oils and waxes such as, for example, myristyl alcohol, 1-pentadecanol, cetyl alcohol, 1-heptadecanol, stearyl alcohol, 1-nonadecanol, arachidyl alcohol, 1-heneicosanol, behenyl alcohol, brassidyl alcohol, lignoceryl alcohol, ceryl alcohol or myricyl alcohol. According to the invention, saturated, unbranched fatty alcohols are preferred. However, unsaturated, branched or unbranched fatty alcohols may also be used as wax component for the purposes of the invention providing they have the required melting point. Other suitable fatty alcohols are the fatty alcohol cuts obtained in the reduction of naturally occurring fats and oils such as, for example, bovine tallow, peanut oil, colza oil, cottonseed oil, soybean oil, sunflower oil, palm kernel oil, linseed oil, castor oil, corn oil, rapeseed oil, sesame oil, cocoa butter and coconut oil. However, synthetic alcohols, for example the linear, even-numbered fatty alcohols from Ziegler's synthesis (Alfols®) or the partly branched alcohols from the oxosynthesis (Dobanols®) may also be used. A preferred embodiment of the composition according to the invention contains at least one fatty alcohol as another wax-like lipid component. $C_{14-22}$ fatty alcohols marketed for example by Cognis Deutschland GmbH under the name of Lanette® 16 ($C_{16}$ alcohol), Lanette® 14 ($C_{14}$ alcohol), Lanette® O ($C_{16/18}$ alcohol) and Lanette® 22 ($C_{18/22}$ alcohol) are particularly suitable for the purposes of the invention. Fatty alcohols give the compositions a dryer feeling on the skin than triglycerides and are therefore preferred to triglycerides.

$C_{14-40}$ fatty acids or mixtures thereof may also be used as wax components. These include, for example, myristic, pentadecanoic, palmitic, margaric, stearic, nonadecanoic, arachic, behenic, lignoceric, cerotic, melissic, erucic and elaeostearic acid and substituted fatty acids such as, for example, 12-hydroxystearic acid, and the amides or monoethanolamides of the fatty acids. This list is meant to be purely exemplary without any limiting character.

Waxes suitable for use in accordance with the present invention are, for example, natural vegetable waxes, such as candelilla wax, carnauba wax, Japan wax, espartograss wax, cork wax, guaruma wax, rice oil wax, sugar cane wax, ouricury wax, montan wax, sunflower wax, fruit waxes, such as orange waxes, lemon waxes, grapefruit wax, bayberry wax, and animal waxes such as, for example, beeswax, shellac wax, spermaceti, wool wax and uropygial fat. According to the invention, it can be of advantage to use hydrogenated or hardened waxes. Natural waxes usable in accordance with the invention also include the mineral waxes, such as ceresine and ozocerite for example, or the petrochemical waxes, for example petrolatum, paraffin waxes and microwaxes. Other suitable wax components are chemically modified waxes, more particularly the hard waxes such as, for example, montan ester waxes, sasol waxes and hydrogenated jojoba waxes. Synthetic waxes usable in accordance with the invention include, for example, wax-like polyalkylene waxes and polyethylene glycol waxes. Vegetable waxes are preferred for the purposes of the invention.

The other wax component may also be selected from the group of wax esters of saturated and/or unsaturated, branched and/or unbranched alkanecarboxylic acids and saturated and/or unsaturated, branched and/or unbranched alcohols, from the group of esters of aromatic carboxylic acids, dicarboxylic acids, tricarboxylic acids and hydroxycarboxylic acids (for example 12-hydroxystearic acid) and saturated and/or unsaturated, branched and/or unbranched alcohols and also from the group of lactides of long-chain hydroxycarboxylic acids. Wax components such as these include, for example, $C_{16-40}$ alkyl stearates, $C_{20-40}$ alkyl stearates (for example Kesterwachs® K82H), $C_{20-40}$ dialkyl esters of dimer acids, $C_{18-38}$ alkyl hydroxystearoyl stearates or $C_{20-40}$ alkyl erucates. Other suitable wax components which may be used with advantage are $C_{30-50}$ alkyl beeswax, tristearyl citrate, triisostearyl citrate, stearyl heptanoate, stearyl octanoate, trilauryl citrate, ethylene glycol dipalmitate, ethylene glycol distearate, ethylene glycol di(12-hydroxystearate), stearyl stearate, palmityl stearate, stearyl behenate, cetearyl behenate and behenyl behenate.

Oil Components

In another preferred embodiment, the compositions according to the invention additionally contain at least one oil component liquid at 25° C. or a mixture of such oil components. The oil component(s) is/are present in a quantity of 1 to 25% by weight, preferably in a quantity of 1 to 15% by weight and more particularly in a quantity of 5 to 15% by weight, based on the composition as a whole.

Suitable oil components are, for example, the classes of compounds mentioned in the following, providing they are liquid at 25° C. These include inter alia Guerbet alcohols based on fatty alcohols containing 6 to 18 and preferably 8 to 10 carbon atoms, esters of linear or branched, saturated or unsaturated $C_{6-22}$ fatty acids with linear or branched, saturated or unsaturated $C_{6-22}$ fatty alcohols, more particularly 2-ethyl hexanol. The following are mentioned by way of example: hexyl laurate, myristyl isostearate, myristyl oleate, cetyl isostearate, cetyl oleate, stearyl isostearate, stearyl oleate, isostearyl myristate, isostearyl palmitate, isostearyl stearate, isostearyl isostearate, isostearyl oleate, oleyl myristate, oleyl isostearate, oleyl oleate, oleyl erucate, erucyl isostearate, erucyl oleate, cococaprylate/caprate. Other suitable esters are, for example, are esters of $C_{18-38}$ alkylhydroxycarboxylic acids with linear or branched, saturated or unsaturated $C_{6-22}$ fatty alcohols, esters of linear and/or branched, saturated and/or unsaturated fatty acids with polyhydric alcohols (for example propylene glycol, dimer diol or trimer triol) and/or Guerbet alcohols, triglycerides or triglyceride mixtures, liquid mono-, di- and triglyceride mixtures, esters of $C_{6-22}$ fatty alcohols and/or Guerbet alcohols with aromatic carboxylic acids, more particularly benzoic acid, esters of $C_{2-12}$ dicarboxylic acids with linear or branched, saturated or unsaturated alcohols containing 1 to 22 carbon atoms or polyols containing 2 to 10 carbon atoms and 2 to 6 hydroxyl groups, vegetable oils, branched primary alcohols, substituted cyclohexanes, linear dialkyl carbonates, Guerbet carbonates based on fatty alcohols containing 6 to 18 and preferably 8 to 10 carbon atoms, esters of benzoic acid with linear and/or branched $C_{6-22}$ alcohols (for example Finsolv® TN), linear or branched, symmetrical or nonsymmetrical dialkyl ethers containing 6 to 22 carbon atoms per alkyl group such as, for example, Di-n-octyl Ether (Cetiol® OE) or ring opening products of epoxidized fatty acid esters with polyols, hydrocarbons, such as paraffin or mineral oils, oligo- or poly-α-olefins.

According to the invention, dialkyl ethers, dialkyl carbonates, triglyceride mixtures and esters of $C_{8-24}$ fatty acids and $C_{8-24}$ fatty alcohols or mixtures of these substances are particularly suitable for use as the oil component. The dialkyl carbonates and dialkyl ethers may be symmetrical or asymmetrical, branched or unbranched, saturated or unsaturated and may be produced by reactions known from the prior art. A preferred embodiment of the invention is characterized by the use of a mixture of oil components which contains esters, dialkyl ethers and triglycerides, but no silicone oils.

According to the invention, other suitable oil components are inter alia hydrocarbons, preferably with a chain length of 8 to 40 carbon atoms. They may be branched or unbranched, saturated or unsaturated. Of these, branched, saturated $C_{8-40}$ alkanes are preferred. Both pure substances and mixtures may be used. The mixtures are normally mixtures of different isomeric compounds. Compositions containing $C_{10-30}$, preferably $C_{12-20}$ and more particularly $C_{16-20}$ alkanes are particularly suitable and, of these, a mixture of alkanes containing at least 10% by weight branched alkanes, based on the total quantity of alkanes, is particularly preferred. The alkanes are preferably branched, saturated alkanes. Mixtures of alkanes containing more than 1% by weight 5,8-diethyl dodecane and/or more than 1% by weight didecene are particularly suitable.

Surface-Active Substances

Another preferred embodiment of the composition according to the invention additionally contains at least one nonionic surfactant which contributes towards stabilizing the formulations according to the invention. The content of nonionic surfactant is determined by the type of formulation, but does not normally exceed 10% by weight. The preferred content is from 0.5 to 10% by weight, preferably from 0.5 to 5% by weight and more particularly from 0.5 to 3% by weight, based on the composition as a whole. Typical examples of nonionic surfactants are fatty alcohol polyglycol ethers, polyglycerol esters, alkylphenol polyglycol ethers, fatty acid polyglycol esters, fatty acid amide polyglycol ethers, fatty amine polyglycol ethers, alkoxylated mono/di/triglycerides, mixed ethers and mixed formals, optionally partly oxidized alk(en)yl oligoglycosides or glucuronic acid derivatives, fatty acid-N-alkyl glucamides, protein hydrolyzates (particularly wheat-based vegetable products), polyol fatty acid esters, sugar esters, sorbitan esters, polysorbates and amine oxides. If the nonionic surfactants contain polyglycol ether chains, they may have a conventional homolog distribution, although they preferably have a narrow-range homolog distribution. In one particularly preferred embodiment, the nonionic surfactant is selected from the group of alk(en)yl oligoglycosides.

Alk(en)yl oligoglycosides are known nonionic surfactants which correspond to formula (I):

$$R^1O\text{-}[G]_p \qquad (I)$$

where $R^1$ is an alk(en)yl group, G is a sugar unit containing 5 or 6 carbon atoms and p is a number of 1 to 10. They may be obtained by the relevant methods of preparative organic chemistry. EP-A1-0 301 298 and WO 90/03977 are cited here as representative of the literature abundantly available on the subject.

The alk(en)yl oligoglycosides may be derived from aldoses or ketoses containing 5 or 6 carbon atoms, preferably glucose. Accordingly, the preferred alk(en)yl oligoglycosides are alk (en)yl oligoglucosides. The index p in general formula (I) indicates the degree of oligomerization (DP), i.e. the distribution of mono- and oligoglycosides, and is a number of 1 to 10. Whereas p in a given compound must always be an integer and, above all, may assume a value of 1 to 6, the value p for a certain alk(en)yl oligoglycoside is an analytically determined calculated quantity which is generally a broken number. Alk (en)yl oligoglycosides having an average degree of oligomerization p of 1.1 to 3.0 are preferably used. Alk(en)yl oligoglycosides having a degree of oligomerization of less than 1.7 and, more particularly, between 1.2 and 1.4 are preferred from the applicational perspective. Alkyl oligoglucosides in which the substituent R' is derived from primary $C_{8-24}$, preferably $C_{12-24}$ and more particularly $C_{16-18}$ alcohols are preferably used in accordance with the invention. Technical mixtures of the alcohols may also be used.

Anionic, cationic and/or amphoteric or zwitterionic surfactants/emulsifiers or a mixture of these surfactants/emulsifiers may also be present as surfactants in the compositions according to the invention.

Typical examples of anionic surfactants are soaps, alkyl benzenesulfonates, alkanesulfonates, olefin sulfonates, alkylether sulfonates, glycerol ether sulfonates, α-methyl ester sulfonates, sulfofatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow-range homolog distribution. Typical examples of cationic surfactants are quaternary ammonium compounds, for example dimethyl distearyl ammonium chloride, and esterquats, more particularly quaternized fatty acid trialkanolamine ester salts. Typical examples of amphoteric or zwitterionic surfactants are alkylbetaines, alkylamidobetaines, aminopropionates, aminoglycinates, imidazolinium betaines and sulfobetaines. The surfactants mentioned are all known compounds. Information on their structure and production can be found in relevant synoptic works. Typical examples of particularly suitable mild, i.e. particularly dermatologically compatible, surfactants are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, α-olefin sulfonates, ether carboxylic acids, alkyl oligoglucosides, fatty acid glucamides, alkylamidobetaines, amphoacetals and/or protein fatty acid condensates, preferably based on wheat proteins.

Another preferred composition is characterized in that it contains the following components: (a) 0.1 to 10% by weight of at least one wax component according to any of claims 1 to 4, (b) 1 to 25% by weight of at least one oil component liquid at 25° C., (c) 0.1 to 5% by weight of a $C_{12-24}$ fatty alcohol or $C_{12-14}$ partial glyceride or a mixture thereof, (d) 0.5 to 10% by weight of a $C_{8-24}$ alkyl oligoglucoside and (e) water. A particularly preferred composition contains (a) 0.5 to 5% by weight of at least one wax component according to any of claims 1 to 4, (b) 5 to 15% by weight of at least one oil component liquid at 20° C., (c) 1 to 5% by weight of a $C_{12-24}$ fatty alcohol or $C_{12-14}$ partial glyceride or a mixture thereof, (d) 0.5 to 5% by weight of a $C_{12-24}$ alkyl oligoglucoside and (e) up to 90% by weight water. According to the invention, esters of pentaerythritol which are obtained by reaction of pentaerythritol with a fatty acid mixture containing 42 to 48% by weight $C_{16}$ fatty acid and 50 to 56% by weight $C_{18}$ fatty acid (rest: $\leq C_{14}$ fatty acids and $>C_{18}$ fatty acids) and which contain 12 to 19% by weight monoester, (b) 25 to 35% by weight diester, (c) 30 to 40% by weight triester and (d) 6 to 11% by weight tetraester represent the preferred wax component (a).

Hydrotropes

Another preferred embodiment of the invention additionally contains at least one compound from the group of hydrotropes. The function of the hydrotrope(s) is to improve flow behavior and sensory profile. Suitable hydrotropes are, for example, ethanol, isopropyl alcohol or polyols. Suitable polyols preferably contain 2 to 15 and more particularly 2 to 6 carbon atoms and at least two hydroxyl groups. According to the invention, glycerol is preferred. The hydrotrope content is from 0.1 to 10% by weight, preferably from 0.5 to 5% by weight and more particularly from 1 to 5% by weight, based on the composition as a whole.

Other Optional Auxiliaries and Additives

Depending on their intended application, the cosmetic formulations contain a number of other auxiliaries and additives such as, for example, thickeners, superfatting agents, stabilizers, polymers, lecithins, phospholipids, biogenic agents, UV protection factors, antioxidants, deodorants, film formers, swelling agents, insect repellents, hydrotropes, solubilizers, preservatives. perfume oils, dyes, etc. which are listed by way of example in the following. The quantities in which the particular additives are used is determined by the intended use.

Suitable thickeners are, for example, Aerosil® types (hydrophilic silicas), polysaccharides, more especially xanthan gum, guar-guar, agar-agar, alginates and tyloses, carboxymethyl cellulose and hydroxyethyl and hydroxypropyl cellulose, polyvinyl alcohol, polyvinyl pyrrolidone and bentonites such as, for example, Bentone® GeIVS-5PC (Rheox).

UV protection factors in the context of the invention are, for example, organic substances (light filters) which are liquid or crystalline at room temperature and which are capable of absorbing ultraviolet radiation and of releasing the energy absorbed in the form of longer-wave radiation, for example heat. UV-B filters can be oil-soluble or water-soluble. Typical UV-A filters are, in particular, derivatives of benzoyl methane. The UV-A and UV-B filters may of course also be used in the form of mixtures, for example combinations of the derivatives of benzoyl methane, for example 4-tert.butyl-4'-methoxydibenzoylmethane (Parsol® 1789) and 2-cyano-3,3-phenylcinnamic acid-2-ethyl hexyl ester (Octocrylene), and esters of cinnamic acid, preferably 4-methoxycinnamic acid-2-ethyl hexyl ester and/or 4-methoxycinnamic acid propyl ester and/or 4-methoxycinnamic acid isoamyl ester. Combinations such as these are often combined with water-soluble filters such as, for example, 2-phenylbenzimidazole-5-sulfonic acid and alkali metal, alkaline earth metal, ammonium, alkylammonium, alkanolammonium and glucammonium salts thereof.

Besides the soluble substances mentioned, insoluble light-blocking pigments, i.e. finely dispersed metal oxides or salts, may also be used for this purpose. Examples of suitable metal oxides are, in particular, zinc oxide and titanium dioxide.

Besides the two groups of primary sun protection factors mentioned above, secondary sun protection factors of the antioxidant type may also be used. Secondary sun protection factors of the antioxidant type interrupt the photochemical reaction chain which is initiated when UV rays penetrate into the skin.

In the context of the invention, biogenic agents are, for example, tocopherol, tocopherol acetate, tocopherol palmitate, ascorbic acid, (deoxy)ribonucleic acid and fragmentation products thereof, β-glucans, retinol, bisabolol, allantoin, phytantriol, panthenol, AHA acids, amino acids, ceramides, pseudoceramides, essential oils, plant extracts, for example prunus extract, bambara nut extract, and vitamin complexes.

Deodorizing components counteract, mask or eliminate body odors. Body odors are formed through the action of skin bacteria on apocrine perspiration which results in the formation of unpleasant-smelling degradation products. Accordingly, suitable deodorizing components are inter alia germ inhibitors, enzyme inhibitors, odor absorbers or odor maskers.

Suitable insect repellents are, for example, N,N-diethyl-m-toluamide, pentane-1,2-diol or 3-(N-n-butyl-N-acetylamino)-propionic acid ethyl ester), which is marketed as Insect Repellent® 3535 by Merck KGaA, and Butylacetylaminopropionate.

A suitable self-tanning agent is dihydroxyacetone. Suitable tyrosine inhibitors which prevent the formation of melanin and are used in depigmenting agents are, for example, arbutin, ferulic acid, koji acid, coumaric acid and ascorbic acid (vitamin C).

Suitable preservatives are, for example, phenoxyethanol, formaldehyde solution, parabens, pentanediol or sorbic acid and the silver complexes known under the name of Surfacine® and the other classes of compounds listed in Appendix 6, Parts A and B of the Kosmetikverordnung ("Cosmetics Directive").

Suitable perfume oils are mixtures of natural and synthetic perfumes. Natural perfumes include the extracts of blossoms, stems and leaves, fruits, fruit peel, roots, woods, herbs and grasses, needles and branches, resins and balsams. Animal raw materials, for example civet and beaver, and synthetic perfume compounds of the ester, ether, aldehyde, ketone, alcohol and hydrocarbon type, are also suitable.

Suitable dyes are any of the substances suitable and approved for cosmetic purposes. Examples include cochineal red A (C.I. 16255), patent blue V (C.I. 42051), indigotin (C.I. 73015), chlorophyllin (C.I. 75810), quinoline yellow (C.I. 47005), titanium dioxide (C.I. 77891), indanthrene blue RS (C.I. 69800) and madder lake (C.I. 58000). These dyes are normally used in concentrations of 0.001 to 0.1% by weight, based on the mixture as a whole.

EXAMPLES

The quantities shown represent % by weight of the commercially available substance in the composition as a whole. C1 is a Comparison Example.

| Commercial Name (INCI) | C1 | 1 |
|---|---|---|
| Emulgade ® PL 68/50 (Cetearyl Glucoside (and) Cetearylalcohol) | 2.7 | 2.7 |
| Pentaerythritol-C18-ester[1] | 1.6 | |
| Pentaerythritol-C16/18-ester[2] | | 1.6 |
| Cetiol ® J600 (Oleyl Erucate) | 3.0 | 3.0 |
| Myritol ® 312 (Caprylic/Capric Triglyceride) | 4.0 | 4.0 |
| Cetiol ® V (Decyl Oleate) | 2.0 | 2.0 |
| Cetiol ® OE (Dicaprylyl Ether) | 2.0 | 2.0 |
| Wacker ® AK 350 (Dimethicone) | 0.5 | 0.5 |
| Glycerol | 3.0 | 3.0 |
| Water, preservative q.s. | ad 100 | |
| Potassium hydroxide | pH 7.0 | |
| Viscosity data[3] at 20° C. [Pa · s] | | |
| After preparation | 12.4 | 12.4 |
| After 1 week | 11.2 | 9.2 |
| After 2 weeks | 10.0 | 7.6 |
| After 4 weeks | 8.0 | 8.4 |
| After 8 weeks | 6.4 | 8.0 |
| After 12 weeks | 2.0 | 8.0 |
| Phase stability[4] at −5° C./20° C./40° C. | | |
| After 1 week | 1/1/1 | 1/1/1 |
| After 2 weeks | 1/1/1 | 1/1/1 |
| After 4 weeks | 1/2/2 | 1/1/1 |
| After 8 weeks | 5/2/3 | 1/1/1 |
| After 12 weeks | 5/5/5 | 1/1/1 |
| Macroscopic[5]/microscopic[6] | | |
| appearance at 20° C. | | |
| After preparation | 1/2 | 1/2 |
| After 1 week | 1/2 | 1/2 |
| After 2 weeks | 2/3 | 1/2 |
| After 4 weeks | 3/3 | 1/2 |
| After 8 weeks | 4/3 | 1/2 |
| After 12 weeks | 4/4 | 1/2 |

-continued

| Commercial Name (INCI) | C1 | 1 |
|---|---|---|
| Sensory evaluation[7] | | |
| After preparation | 1 | 1 |
| After 12 weeks | 3 (flat) | 1 |

[1] Ester of pentaerythritol containing >90% by weight $C_{18}$ fatty acid
[2] Ester of pentaerythritol which is obtained by reaction of 1 mol pentaerythritol with ca. 2 mol of a fatty acid mixture of 42 to 48% by weight $C_{16}$ fatty acid and 50 to 56% by weight $C_{18}$ fatty acid (rest: $\leq C_{14}$ fatty acids and $>C_{18}$ fatty acids), has the following ester distribution: 12 to 19% by weight monoesters, (b) 25 to 35% by weight diesters, (c) 30 to 40% by weight triesters and (d) 6 to 11% by weight tetraesters, and contains less than 0.3% by weight $C_{17}$ fatty acid acyl groups.
[3] Viscosity measurements: Brookfield RVF, spindle 5, 10 r.p.m., 23° C.
[4] Evaluation criteria for visual phase stability: 1 = stable; 2 = slight separation; 3 = separation; 4 = distinct separation; 5 = separation
[5] Evaluation criteria for visual macroscopic appearance: 1 = smooth and shiny; 2 = smooth and flat; 3 = flat; 3 = coarse structure; 4 = visible recrystallizates. The formulations were evaluated after they had been brought to room temperature.
[6] Evaluation criteria for microscopic appearance: 1 = mean particle size $\leq 1$ μm; 2 = mean particle size 1-4 μm; 3 = mean particle size 4-13 μm; 4 = mean particle size 13-20 μm; 5 = mean particle size 20-50 μm. The particle size of the test emulsion was visually compared with the particle size of standard emulsions. To determine the particle size of the standard emulsions, a diffraction pattern is prepared by laser diffraction. The particle sizedistribution is then calculated from the light intensities of the diffraction patterns using the Fraunhofer theory (Sympatec Helos)
[7] Sensory evaluation criteria Test group: 10 experienced and trained volunteers; 1 = very high acceptance; 2 = average acceptance; 3 = unacceptable 10 μl of the above compositions brought beforehand to 20° C. were applied by micropipette to the hair-free side of the forearm of the volunteers and rubbed in with the fingers of the hands of the contralateral side. The sensory profile was evaluated during and after absorption. The sensory test was conducted on 10 volunteers, as described in the book "Cosmetic Lipids and the Skin Barrier" (Marcel Dekker, New York, 2002; Ed.: Thomas Förster, pp. 319-352).

Table 2

The figures shown represent % by weight of the commercially available substance in the composition as a whole. C2 to C4 are Comparison Examples.

TABLE 2

The figures shown represent % by weight of the commercially available substance in the composition as a whole. C2 to C4 are Comparison Examples.

| Commercial Name (INCI) | C2 | C3 | C4 | 2 | 3 |
|---|---|---|---|---|---|
| Emulgade ® PL 68/50 (Cetearyl Glucoside, Cetearylalcohol) | 2.7 | 2.7 | 2.7 | 2.7 | 2.7 |
| Pentaerythrityl Distearate[1] | | | | 1.6 | 1.6 |
| Lanette ® O (Cetearylalcohol) | 1.6 | 1.6 | | | |
| Cutina ® GMS-V (Glyceryl Monostearate) | | | 1.6 | | |
| Cetiol ® J600 (Oleylerucale) | 3.0 | 3.0 | 3.0 | 3.0 | 3.0 |
| Myritol ® 312 (Caprylic/Capric Triglyceride) | 4.0 | 4.0 | 4.0 | 4.0 | 4.0 |
| Cetiol ® V (Decyl Oleate) | 2.0 | 2.0 | 2.0 | 2.0 | 2.0 |
| Cetiol ® OE (Dicaprylyl Ether) | 2.0 | 2.0 | 2.0 | 2.0 | 2.0 |
| Wacker-Silikonöl AK ® 350 (Dimethicone) | 0.5 | | 0.5 | 0.5 | |
| Glycerol | 3.0 | 3.0 | 3.0 | 3.0 | 3.0 |
| Water | ad 100 | ad 100 | ad 100 | ad 100 | ad 100 |
| Sensory evaluation[2] | | | | | |
| Spreadability | 0 | 0 | 0 | + | ++ |
| White residue | + | 0 | ++ | ++ | + |
| Absorption | – | – | + | ++ | ++ |
| Tackiness | 0 | 0 | + | + | + |

TABLE 2-continued

The figures shown represent % by weight of the commercially available substance in the composition as a whole. C2 to C4 are Comparison Examples.

| Commercial Name (INCI) | C2 | C3 | C4 | 2 | 3 |
|---|---|---|---|---|---|
| Smoothness | 0 | – | 0 | ++ | ++ |
| Softness | – | – | + | ++ | ++ |
| Acceptance | – | – | + | + | ++ |

[1] Ester of pentaerythritol which is obtained by reaction of 1 mol pentaerythritol with ca. 2 mol of a fatty acid mixture of 42 to 48% by weight $C_{16}$ fatty acid and 50 to 56% by weight $C_{18}$ fatty acid (rest: $\leq C_{14}$ fatty acids and $>C_{18}$ fatty acids), has the following ester distribution: 12 to 19% by weight monoesters, (b) 25 to 35% by weight diesters, (c) 30 to 40% by weight triesters and (d) 6 to 11% by weight tetreesters, and contains less than 0.3% by weight $C_{17}$ fatty acid acyl groups.
[2] Sensory evaluation criteria by comparison with formulations C2-C4
Test group: 10 experienced and trained volunteers; ++ = excellent; + = very good; 0 = good; – = moderate; — = poor; procedure as described in Point 7) below Table 1.

What is claimed is:

1. A fatty acid ester mixture of pentaerythritol, wherein the fatty acid has 6 to 22 carbon atoms, the esters have a ratio by weight of $C_{16}/C_{18}$ fatty acid of about 0.7 to 0.9, and wherein said ester mixture contains less than 0.3% by weight of esters containing $C_{17}$ fatty acid acyl groups, and has a melting point of at least 30° C., with a percentage content of (a) about 12% to about 19% by weight monoesters, (b) about 25% to about 35% by weight diesters, (c) about 30% to about 40% by weight triesters, and (d) tetraesters,
wherein said fatty acid ester mixture of pentaerythritol is incorporated as a wax component in a cosmetic and/or pharmaceutical composition.

2. The fatty acid ester mixture of claim 1, wherein the fatty acid is a mixture containing about 40% to about 50% by weight of a $C_{16}$ fatty acid and about 45% to about 55% by weight of a $C_{18}$ fatty acid.

3. A cosmetic and/or pharmaceutical composition comprising: a fatty acid ester mixture of pentaerythritol, wherein the fatty acid has 6 to 22 carbon atoms, the esters have a ratio by weight of C16/C18 fatty acid of about 0.7 to 0.9, and wherein said ester mixture contains less than 0.3% by weight of esters containing C17 fatty acid acyl groups, and has a melting point of at least 30° C., with a percentage content of (a) about 12% to about 19% by weight monoesters, (b) about 25% to about 35% by weight diesters, (c) about 30% to about 40% by weight triesters, and (d) tetraesters.

4. The composition according to claim 3, wherein said $C_{6-22}$ fatty acid is present as a mixture and comprises about 40% to about 50% by weight of a $C_{16}$ fatty acid and about 45% to about 55% by weight of a $C_{18}$ fatty acid.

5. The composition according to claim 3, wherein said wax ester mixture is present in a quantity of about 0.1% to about 20% by weight.

6. The composition according to claim 3, further comprising an additional wax component.

7. The composition according to claim 6, wherein said wax component is selected from the group consisting of $C_{12-24}$ fatty alcohols, $C_{12-24}$ partial glycerides and mixtures thereof.

8. The composition according to claim 3, further comprising at least one nonionic surfactant.

9. The composition according to claim 8, wherein said nonionic surfactant is selected from the group consisting of alkyl oligoglycosides, alkenyl oligoglycosides and mixtures thereof.

10. The composition according to claim 3, further comprising at least one oil component which is liquid at 25° C.

11. The composition according to claim 3, comprising:
(a) about 0.1% to about 10% be weight of said wax ester mixture;
(b) about 1% to about 25% by weight of at least one oil component which is liquid at 25° C.;
(c) about 0.1% to about 5% by weight of a wax component selected from the group consisting of $C_{12-24}$ fatty alcohols, $C_{12-24}$ partial glycerides, and mixtures thereof;
(d) about 0.5% to about 10% by weight of a $C_{8-24}$ alkyl oligoglucoside; and
(e) water.

12. The fatty acid ester mixture of claim 1, wherein the fatty acid contains 6 to 22 carbon atoms and comprises unbranched fatty acids.

13. The fatty acid ester mixture of claim 1 wherein said fatty acid comprises a mixture of $C_{6-22}$ fatty acids.

14. The fatty acid ester mixture of claim 12 wherein said fatty acid comprises a mixture of $C_{6-22}$ fatty acids.

* * * * *